United States Patent
Sunil Kumar et al.

(10) Patent No.: US 9,456,994 B2
(45) Date of Patent: Oct. 4, 2016

(54) EFFICIENT PROCESS FOR THE PREPARATION OF LYCOPENE CONTAINING OLEORESIN AND LYCOPENE CRYSTALS FOR HUMAN CONSUMPTION

(71) Applicant: OMNIACTIVE HEALTH TECHNOLOGIES LIMITED, Thane (IN)

(72) Inventors: T. K. Sunil Kumar, Thane (IN); P. A. Sherena, Thane (IN)

(73) Assignee: OmniActive Health Technologies Limited, Mumbai (IN)

( * ) Notice: Subject to any disclaimer, the term of this patent is extended or adjusted under 35 U.S.C. 154(b) by 0 days.

(21) Appl. No.: 14/345,467

(22) PCT Filed: Sep. 17, 2012

(86) PCT No.: PCT/IB2012/001806
§ 371 (c)(1),
(2) Date: Mar. 18, 2014

(87) PCT Pub. No.: WO2013/041935
PCT Pub. Date: Mar. 28, 2013

(65) Prior Publication Data
US 2015/0004236 A1  Jan. 1, 2015

(30) Foreign Application Priority Data

Sep. 19, 2011 (IN) .......................... 2646/MUM/2011

(51) Int. Cl.
| A61K 31/01 | (2006.01) |
| C07C 7/10 | (2006.01) |
| C07C 7/148 | (2006.01) |
| A23L 1/212 | (2006.01) |
| A23L 1/30 | (2006.01) |

(52) U.S. Cl.
CPC .............. *A61K 31/01* (2013.01); *A23L 1/2121* (2013.01); *A23L 1/3002* (2013.01); *C07C 7/10* (2013.01); *C07C 7/14891* (2013.01); *C07B 2200/13* (2013.01)

(58) Field of Classification Search
None
See application file for complete search history.

(56) References Cited

U.S. PATENT DOCUMENTS

| 5,837,311 A | 11/1998 | Zelkha et al. |
| 5,858,700 A | 1/1999 | Ausich et al. |
| 5,871,574 A | 2/1999 | Kawaragi et al. |
| 5,897,866 A | 4/1999 | Bombardelli et al. |
| 5,965,183 A | 10/1999 | Hartal et al. |
| 6,235,315 B1 | 5/2001 | Runge et al. |
| 6,261,598 B1 * | 7/2001 | Runge .................. A23K 1/1603 424/401 |
| 6,331,652 B1 | 12/2001 | Konya et al. |
| 2003/0180366 A1* | 9/2003 | Kirschner .............. A61K 47/12 424/489 |
| 2004/0024275 A1* | 2/2004 | Vuong ................... A23L 1/3002 585/351 |
| 2011/0008495 A1* | 1/2011 | Paul ....................... A23L 1/3002 426/72 |

FOREIGN PATENT DOCUMENTS

| CN | 1965693 | 5/2007 |
| CN | 101534845 | 9/2009 |
| EP | 1 103 579 | 5/2001 |
| EP | 1 384 472 | 1/2004 |
| JP | 2002-193850 | 7/2002 |
| JP | 2007-269631 | 10/2007 |
| WO | WO96/13178 | * 5/1996 |
| WO | 97/48287 | 12/1997 |

OTHER PUBLICATIONS

Boileau et al., Cis-Lycopene is more Bioavailable than Trans-Lycopene in Vitro and In Vivo in Lymph-Cannulated Ferrets, J.Nutrition.129, 1176-1181(1999).
Shi, et al., Lycopene in Tomatoes: Chemical and Physical Properties Affected by Food Processing:, Crit. Rev. Biotechnol. 20, 293-334 (2000).
Wang, et al., "Tomato pulp as source for the production of lycopene powder containing high proportion of cis-isomers", Eu. Fd. Res. Technol—222, 347-355 (2006).
Unlu et al., "Lycopene from heat-induced cis-isomer-rich tomato sauce is more bioavailable than from all-trans-rich tomato sauce in human subjects", Brit. J. Nutr. 98,140-146, 2007.
Ollanketo et al., "Supercritical carbon dioxide extraction of lycopene in tomato skins", Eu.Fd.Res.Technol, 212, 561-565 (2001).
Salud Gomez-Prieto et al., "Supercritical Fluid Extraction of all-trans-Lycopene from Tomato" J. Agr. Fd. Chem. 51, 3-7 (2003).
Kun, et al., "Lycopene: Its Properties and Relationship to Human Health", Fd. Rev. International. 22, 309-333 (2006).

(Continued)

Primary Examiner — Johann R Richter
Assistant Examiner — Katherine Peebles
(74) Attorney, Agent, or Firm — Hamre, Schumann, Mueller & Larson, P.C.

(57) ABSTRACT

The present invention provides a process for the preparation of lycopene containing oleoresin and lycopene crystals for human consumption. The present invention provides an efficient process for the preparation of lycopene crystals from lycopene containing oleoresin with at least 85% by weight lycopene, containing at least 90% by weight trans-lycopene and trace amounts of cis-lycopene and other carotenoids. The production of commercial grade lycopene crystals with high content of trans-lycopene makes it ideal and suitable for human consumption, use as an anti-oxidant, for applications in prevention of cancer and macular degenerative diseases, as an anti-oxidant, and as a food/feed colorant. The process is simple, convenient, economical and commercially feasible.

13 Claims, No Drawings

(56) References Cited

OTHER PUBLICATIONS

Chasse et al., "An ab initio computational study on selected lycopene isomers", J. Mol. Struc. (Theochem) 571, 27-37 (2001).
Rao, et al., "Lycopene", Adv. Fd .and Nutr. Res. 51, 99-164 (2006).
Shi et al., "Lycopene in tomatoes: Chemical and physical properties affected by food processing", Critical Reviews in Food Science and Nutrition, 40,1-42, (2000).
Micozzi et al., "Carotenoid analysis of selected raw and cooked foods associated with lower risk of cancer", Journal of Natl. Cancer Institute, 82, 282-28 (1990).
Kristenson et al., "Antioxidant state and mortality from coronary heart deceases in Lithuanian and Swedish men: Concomitant cross sectional study of men aged 50", Brit. Med. J. 314, 629-633 (1997).
Kohlmeir et al., "Lycopene and Myocardial Infarction risk in the EURAMIC study", American Journal of Epidemiology, 146, 618-626 (1997).
Stahl et al., "Uptake of lycopene and its geometrical isomers is greater from heat-processed than from unprocessed tomato juice in humans", J. Nutrition, 122, 2162-2166 (1992).
Jackson, M.J., "The assessment of bioavailability of micronutrients; Introduction", European Journal of Clinical Nutrition, 51, S1-S2 (1997).
Gartner et al., "Lycopene is more bioavailable from tomato paste than from fresh tomatoes", Amer. Journal of Clinical Nutrition 56, 116-122 (1997).
Brown et al., "Plasma carotenoids in normal men after a single ingestion of vegetable or purified $\beta$-carotene[1-3]", Journal of Clinical Nutrition 49, 1258-1265 (1989).
Sadler et al., "Rapid extraction of $\beta$-carotene and lycopene from reconstituted tomato paste and pink grape fruit homogenates", Journal of Food Science, 55, 1460-146 (1990).
Benthin et al., "Pressurized liquid extraction of medicinal plants", J. Chrom. ,A. 831, 211-219 (1999).
Cole et al., "Stability of lycopene. I.—Degradation by oxygen", J. of Science food Agric, 8, 360-365 (1957).
Shi, et al., "Lycopene degradation and isomerisation in tomato dehydration", Food Res. Intl. 32, 15-31 (1999).
W.A. Schulte, "Efficiency of chemical and physical tomato peeling systems and their effects on canned products quality", Ph.D. Thesis, p. 199, 1965, Ohio State Univ.
Schierle et al., "Content and isomeric ratio of lycopene in food and human blood plasma", Food Chem. 59(3), 459-465 (1996).
Zhou, et al., "Study on extracting lycopene by saponification", Science and Technology of Cereals, Oils and Foods, 17, 2009, 56-59—Abstract.
European Office Action, issued in the corresponding European patent application No. EP 12 769 716.7, dated Nov. 10, 2015, 6 pages.
Chinese Office Action, issued in the corresponding Chinese patent application No. 2012800454766, dated Jun. 3, 2015, 12 pages.
Japanese Office Action, issued in the corresponding Japanese Application No. 2014-530329, dated Oct. 29, 2015, 10 pages.
Chinese Office Action, issued in the corresponding Chinese patent application No. 2012800454766, dated Jan. 5, 2016, 11 pages.

* cited by examiner

EFFICIENT PROCESS FOR THE PREPARATION OF LYCOPENE CONTAINING OLEORESIN AND LYCOPENE CRYSTALS FOR HUMAN CONSUMPTION

FIELD OF THE INVENTION

The present invention relates to an efficient process for the preparation of lycopene containing oleoresin and lycopene crystals for human consumption. More particularly, the present invention relates to a process for the preparation of tomato oleoresin and lycopene crystals enriched with high content of trans-lycopene. The said process comprises preparation of tomato oleoresin from tomato fruits and its products and the preparation of lycopene crystals from tomato oleoresin. High content of trans-lycopene makes it suitable for use as an anti-oxidant, human nutritional supplements, for applications in prevention of cancer and heart related diseases and as a food/feed colorant.

BACKGROUND OF THE INVENTION

Lycopene is a carotenoid that is found in red fruits, such as tomatoes and watermelons. Carotenoids are natural pigments that act as antioxidants for the body. Antioxidants serve to lessen the effects of free radicals, which are attributed to be responsible in damaging the cells in the body.

Lycopene, a polyene hydrocarbon, an acyclic open chain unsaturated carotenoid having 13(C—C) double bonds, of which 11 are conjugated double bonds arranged in a linear array. Two central —$CH_3$ groups are in the 1, 6 position, while the remaining —$CH_3$ are in 1, 5 position relative to each other. Color and antioxidant properties of lycopene are due to an extended system of conjugated double bonds.

parts. Some of the differences observed in cis-isomers are decreased colour intensity, lower melting points, smaller extinction coefficients, and a blue shift in the ultraviolet spectrum known as cis-peaks which help in identification. The cis-isomers are more polar, more soluble in oil and hydrocarbon solvents and less prone to crystallization due to structural configurations.

During tomato processing, lycopene may also undergo degradation due to exposure to heating in the presence of metallic ions such as cupric, ferric, etc. and oxygen. During the product storage, the conversion of lycopene cis-isomer to trans-isomer can occur because cis-isomers are unstable whereas trans-isomers are stable in the ground state. Cis-isomers of lycopene are also known to be more soluble in bile acid micelles and may be preferentially incorporated into chylomicrons when compared to trans-lycopene. (Boileau et al., J. Nutrition. 129, 1176-1181(1999).

It is likely that there is an in-vivo isomerisation of trans- to cis-lycopene within the body. Another possibility is cis-isomers are more bio-available than trans-form as reported in the case of consumption of heat processed tomato products containing higher amounts of cis-lycopene compared to fresh tomato products having largely trans-lycopene [Shi and Maguer, Crit. Rev. Biotechnol. 20, 293-334 (2000)]. Tomato pulp powder and tomato pulp waste obtained from heat processed tomato at 82 degree C. and removing the juice showing cis-lycopene constituting around 56.8% of total lycopene and it may be a potential source for preparing cis-lycopene enriched tomato oleoresin [Wang and Chen. Eu. Fd. Res. Technol-222, 347-355 (2006)]. There is evidence that cis-lycopene is more bio-available than trans-lycopene (Un Lu et al., Brit. J. Nutr. 98, 140-146, 2007).

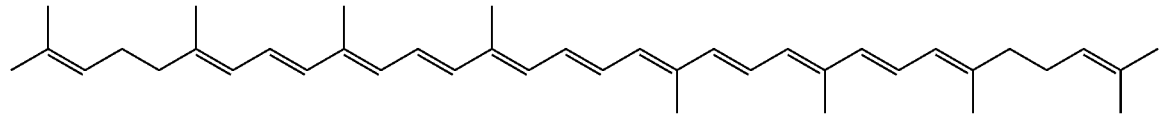 [SMILES: CC(C)=CCC/C(C)=C/C=C/C(C)=C/C=C/C(C)=C/C=C/C=C(C)/C=C/C=C(C)/C=C/C=C(\C)CCC=C(C)C]

Lycopene gets its name from the species classification of tomato, *Lycopersicon esculentum*. It is the principal hydrocarbon carotenoid in tomatoes with lesser amounts of other carotenoids. The composition of carotenoids in tomato fruits are: lycopene (C40H56), 80-90%; α-carotene (C40H56), 0.03%; β-carotene (C40H56), 3-5%; γ-carotene (C40H56), 1-2%, phytoene, (C40H64), 5.6-10%; phytofluene (C40H64), 2.5-3%; neurosprene (C40H64), 7-9% and lutein (C40H58), 0.011-1.1% (Gross. J, 1987, *Pigments in Fruits*, Academic Press, London)

The antioxidant activity of lycopene is due to its ability to trap peroxy radicals. It exists in a variety of geometric isomers such as: all-trans, mono-cis, and poly-cis forms. In nature, lycopene exists in all-trans form and seven of these bonds can isomerise from the trans-form to mono or poly-cis form under the influence of heat, light or certain chemical reactions. The all-trans-isomer is the most predominant isomer in fresh tomatoes and is the most thermodynamically stable form. Lycopene undergoes trans- to cis-isomerisation during processing and storage. In various tomato based foods, trans-isomer is 35-96%, 5-cis-isomer is 4-27%, 9-cis- and 15-cis isomer with considerably lower amounts.

Cis-isomers of lycopene have physical and chemical properties distinctly different from their all-trans counter- Supercritical carbon dioxide extraction of lycopene in tomato skins showed good recovery of total lycopene and ethanol and acetone were used as modifiers. The stability of lycopene stored in solvent was improved through the addition of alpha-tocopherol or rosemary extract [Ollanketo et al., Eu. Fd. Res. Technol, 212, 561-565(2001)].

A procedure is described for the supercritical fluid extraction of all-trans lycopene from dried and powdered tomato skins using carbon dioxide, density 0.9 g/ml, resulting in 88% all-trans-lycopene in the extract [Salud Gomez-Prieto et al., J. Agr. Fd. Chem. 51, 3-7 (2003)]. The study showed that the extraction pressure and the SCF carbon dioxide density are the determining factors assisting in preferential solubility of cis or trans-isomer of lycopene.

In human plasma, lycopene is an isomeric mixture, consisting of at least 60% of the total lycopene as cis-isomers [Yang Kun et al., Lycopene: its properties and relationships to human health; Fd. Rev. International. 22, 309-333 (2006)]. The isomers such as all-trans-; 5-cis-; 9-cis- and 13-cis-lycopene were identified in plasma with configurational stability sequence being 5-cis→all-trans→9-cis→13-cis→15-cis-lycopene.

However, in the computational model study 5-cis-lycopene had the highest antioxidant property as indicated by the ionization potential, the sequence being 5-cis→9-cis→7-cis→13-cis→15-cis→all-trans-lycopene [Chasse et al., *J. Mol. struc. (Theochem)* 571, 27-37 (2001); cited in *Adv. Fd. and Nutr. Res.* 51, 99-164 (2006), Rao et al.]

Most stability studies on lycopene in food system concerns degradation. Lycopene may be partially destroyed in processed tomato products by heating in the presence of metallic ions or oxygen. Lycopene may be expected to undergo at least two changes during tomato processing, isomerisation and oxidation. Lycopene isomerisation can take place during processing. On the other hand, the conversion of cis-form to trans-form can occur during storage [John Shi et al., *Lycopene in tomatoes: Chemical and physical properties affected by food processing*, Critical reviews in food science and nutrition, 40, 1-42, (2000)].

Lycopene acts as a preventive agent for cancer. Lycopene is important, because it appears to provide protection against prostate cancer, lung cancer and a broad range of epithelial cancers [Micozzi et al., *Carotenoid analysis of selected raw and cooked foods associated with lower risk of cancer*, Journal of Natl. Cancer Institute, 82, 282-28 (1990)]. The intake of lycopene has been found to be associated with reduced risk of cancers of other sites such as digestive tract, pancreas and bladders. It was found that women with higher levels of blood lycopene had consumed higher levels of lycopene and vitamin A and had one third less chance of developing cancer.

Lycopene consumption obtained from fruits and vegetables may reduce likelihood of developing heart disease. It prevents oxidation of low density lipoproteins, cholesterol and reduces the risk of developing atherosclerosis and coronary heart disease. [Kristenson et al., *Antioxidant state and mortality from coronary heart deceases in Lithuanian and Swedish men: Concomitant cross sectional study of men aged 50*, Brit. Med. J. 314, 629-633 (1997); Kohlmeir et al., *Lycopene and Myocardial Infarction risk in the EURAMIC study*, American Journal of Epidemiology, 146, 618-626 (1997)]

Bio-availability is defined as the fraction of an ingested nutrient that is available to the body through absorption for utilization in normal physiological functions and for metabolic process.

The composition and structure of food have an impact on bio-availability of lycopene, which may affect the release of lycopene from the tomato tissue matrix. Cooking or fine grinding of foods could increase the bio-availability by disrupting or softening plant cell walls and disrupting lycopene-protein complexes. Thermal processing such as cooking and mechanical texture disruption such as chopping are convenient ways to enhance bio-availability by breaking down study cell wall structures, disrupting chromoplast membranes, and reducing cellular integrity thus making lycopene more accessible. It was found that 20-30% of total lycopene consisted of cis-isomers when tomatoes were heated to 100° C. for 1 hour. [Stahl et al., *Uptake of lycopene and its geometrical isomers is greater from heat processed than from unprocessed tomato juice in humans*, J. Nutrition, 122, 2162-2166 (1992)].

Lycopene bio-availability from tomato based food is significantly higher than from fresh tomatoes; co-ingested with oil. Thermal treatment and oil medium are required to extract lycopene into the lipophobic phase. It was assumed that heating tomato juice in the presence of corn oil for 1 hour converts lycopene from the trans- to cis-form, thereby increasing the level absorption by the human body.

Various dietary fibres reduce the bio-availability. Pectin, a typical dietary fibre affected the absorption of dietary carotenoid in humans. High-methoxy pectin is associated with the hypocholesterolemic effect of dietary fibres and low absorption promoting high viscosity condition.

Absorption of lycopene seemed to be more efficient at lower dosage and lycopene ingested with β-carotene was absorbed more than when ingested alone. A strong decrease in serum lycopene levels were seen after high dose β-carotene supplementation. [Jackson, M. J., *The assessment of bio-availability of micro-nutrients; Introduction*, European Journal of Clinical Nutrition, 51, S1-S2 (1997)]

Food processing may improve the availability of lycopene. The lycopene bio-availability from tomato based food may be enhanced in two ways; extraction of lycopene from the food matrix into the lipophilic phase and thermal process and mechanical disruption of tomato tissue cells. Lycopene in a lipid medium is more bio-available than in fresh tomatoes. Extensive cooking could also destroy lycopene. Optimum processing technology parameters should be found to maximize destruction of the matrix and minimize the destruction of lycopene [Gartner et al., *Lycopene is more bio-available from tomato paste than from fresh tomatoes*, Amer. Journal of Clinical Nutrition 56, 116-122 (1997); Brown et al., *Plasma carotenoids in normal men after a single ingestion of vegetable or purified beta-carotene*, Journal of clinical Nutrition 49, 1258-1265 (1989)].

Lycopene is lipo-soluble; it is usually extracted with a solvent such as chloroform, hexane, acetone, benzene, petroleum ether or carbon disulphide, however a safe solvent is preferred. In cases where a solvent extraction may be slow and incomplete, efficient mechanical grinding of the material is used to facilitate the complete extraction. Dehydrated material may be extracted with water immiscible solvents. Moistening of the dehydrated material prior to solvent extraction is necessary to get complete extraction. Because of sensitivity, extraction is done in dim light and inert atmosphere. To avoid oxidation and isomerisation during extraction, anti-oxidant such as quinol and neutralizing agent such as calcium hydroxide may be added. Extracted sample should be stored in dark under nitrogen in the freezer (−20° C.).

After extraction, saponification is the most effective method of removing unwanted lipids, chlorophylls and other impurities. Further purification and crystallization of the product can be obtained by fractional crystallization from petroleum ether or acetone at low temperature. Some rapid and efficient method for lycopene analysis and identification have been developed using microwave-solvent extraction, pressurized accelerated solvent extraction technologies in which lycopene recoveries from tomatoes ranged from 98.0-99.6%. [Sadler et al., *Rapid extraction of beta-carotene and lycopene from reconstituted tomato paste and pink grape fruit homogenates*, Journal of Food Science, 55, 1460-146 (1990); Benthin et al., *Pressurized liquid extraction of medicinal plants*, J. Chrom., A. 831, 211-219 (1999)]

The determination of lycopene content in tomato and tomato based foods can be carried out by physical and chemical methods. Physical methods are based on the relation of colour parameters with lycopene concentration of the samples. In chemical analysis lycopene is extracted from the tomato tissues and quantified.

Colour measurement has been a convenient and less tedious method for assessing the quality than the chemical analysis method. The deterioration in a quality may be due to the loss of natural pigment. The measurement of chromaticity values with a colorimeter would be useful if it could accurately estimate lycopene concentration in tomato samples after harvest and processing. It will not predict lycopene concentration accurately enough to substitute for chemical extraction analysis.

Spectrophotometric methods: Hexane and acetone are used for extraction of lycopene from tomato tissues and the absorbance is measured at 460-470 nm. A pure sample is necessary for calibration curves.

HPLC method: Reverse phase HPLC method using C18 stationary phase allows for the partial separation of cis- and trans-isomers of pro-vitamin A carotenoids. Mobile phase: Acetonitrile/THF 85/15 diluents IPA/THF 80/20+0.5% BHT. Flow rate 1.5 ml/minute. Run time for 20 minutes.

For processing, tomatoes are washed, sorted and sliced. Sliced tomatoes undergo a hot or cold break method for juice preparation. Juice from tomatoes is usually obtained using screw or paddle extractors. In the manufacturing of other tomato products such as pulp, puree, paste and ketchup, tomato juice is concentrated with steam coils or vacuum evaporators. For canned tomatoes, sliced or whole tomatoes are retorted. For dried, tomato undergoes dehydration methods. Degradation and colour loss may precede and tomato products are affected by a number of factors. The main cause of lycopene degradation is isomerisation and oxidation.

In tomato, the outer pericarp has the highest lycopene and other carotenoids content and the outer wall and the lobular contents have the highest carotene. Tomato skin contains 12 mg lycopene/100 g, while mature tomato contains 3.4 mg lycopene/100 g. The concentration of lycopene in tomato skin is about 3 times higher than in mature tomatoes. Skin and the pericarp of tomato fruits are rich in lycopene. Most of the lycopene is found attached to the insoluble fibre portion of the tomatoes.

Chemical and physical properties of lycopene: melting point—172-175° C.; solubility-soluble in chloroform, hexane, benzene, carbon disulphide, acetone, petroleum ether; sensitivity-light, oxygen, high temperature, acids, metallic ions such as Cu (II), Fe (III) catalyse its oxidation. $\lambda$ max (trans)-lycopene, 446 nm (E1%-2250), 472 nm (E1%-3450), 505 nm (E1%-3150)

The deterioration in colour occurs during the processing of various tomato products resulting from exposure to air at high temperature during processing causing naturally occurring all trans-lycopene to be isomerised and oxidized. Coupled with exposure to oxygen and light, heat treatments that disintegrate tomato tissues can result in the destruction of lycopene. These changes are mainly due to heat stress imposed by the relatively harsh thermal process required for the shelf life stability of the processed tomato products.

Temperature affects the nature and extent of lycopene breakdown. Oxidative degradation of lycopene at 50 degrees C. leads to fragmentation of molecules giving acetone, methyl heptanone, levulinic aldehyde and probably glyoxal as products. Loss of lycopene can occur when the holding time at high temperature is long. Length of heating is a critical factor in controlling the degradation of lycopene. It appears that de-aeration and high temperature-short duration heat treatment can have beneficial effects on the retention of colour quality.

The most important contributing factor for the oxidative destruction of lycopene is the availability of oxygen. More than 30% of lycopene is degraded when heated at 100 degree. C in the presence of oxygen, while 5% was lost in the presence of carbon dioxide. [Cole et al., *Stability of lycopene. I. Degradation by oxygen, J. of Science food Agric,* 8, 360-365 (1957)]. The magnitude of lycopene destruction by exposure to increased lighting is less compared to the increased temperature.

The dehydration of tomato slices is carried out at high temperature over an extended period under vacuum. The general tendency of lycopene retention in samples decreases slightly during dehydration. During osmotic dehydration, lycopene content remains constant. The explanation is that the sugar solution in osmotic dehydration keeps oxygen away from tomatoes and reduces oxidation of lycopene at low operating temperatures. Heat treatment disintegrates tomato tissues and increased exposure to oxygen and light, which resulted in the destruction of lycopene.

Total Lycopene and cis-isomer content in the dehydrated tomato samples [Shi, et al., *Lycopene degradation and isomerisation in tomato dehydration, Food Res. Intl.* 32, 15-31 (1999)]

| Sample | Total lycopene (mcg/g dry basis) | Lycopene loss (%) | All-trans (%) | Cis-Isomer (%) |
| --- | --- | --- | --- | --- |
| Fresh tomato | 775 | 0 | 100 | 0 |
| Osmotic treatment | 775 | 0 | 100 | 0 |
| Osmo-Vac dried | 737 | 2.4 | 93.5 | 6.50 |
| Vac-dried | 731 | 3.2 | 89.9 | 10.10 |
| Air-dried | 726 | 3.90 | 84.4 | 16.6 |

Peeling is an important operation in tomato processing. Chemical treatment includes lye peeling in a hot solution of sodium hydroxide or calcium chloride.

Physical treatment includes steam peeling by high pressure or superheated steam. New peeling methods such as cryogenic scalding with liquid nitrogen, liquid air or Freon-12 or IR peeling with infrared radiation as heat source. During lye peeling, the hot solution dissolves the epicuticular waxes, penetrates the epidermis, digests the middle lamella, cell walls and causes separation of skin. The concentration of lye solution and temperature used range from 8-25 degree C. and from 60-100 degree C. depending on the cultivar and fruit maturity. With steam peeling, tomatoes are exposed to live steam long enough to loosen the peel but not so long as to cause flush softening or cooking Both chemical and steam peeling cause relatively high losses of edible parts of the outer pericarp layer of tomato fruits. Schulte (1965) found that peeling tomatoes with the infrared method produce a peel loss of 5.30% while steam method had a peel loss of 7.50% (W. A. Schulte, Efficiency of chemical and physical tomato peeling systems and their effects on canned products quality, Ph.D. Thesis, p. 199, 1965, Ohio State Univ. USA) The wastes during tomato processing are mainly seeds, pericarp tissues and skin residues. The epidermal area of tomatoes contains more than 80-90% of total lycopene in tomatoes. It is clear that large quantity of lycopene is normally discarded as tomato processing waste. This waste is an important source of lycopene in the food industry.

Reduction of lycopene content and trans-cis-isomerisation results in reduction biological property.

| Sample | Total lycopene mg/100 g | All-trans, % | 5-cis, % | 9-cis, % | 13-cis, % | other Cis-% |
|---|---|---|---|---|---|---|
| Tomato paste (Italy) | 52 | 96 | 4 | <1 | <1 | <1 |
| Tomato paste (Germany) | 3.7 | 91 | 5 | 1 | 2 | <1 |
| Tomato Ketchup (Italy) | 9.5 | 88 | 7 | 2 | 3 | 1 |
| Tomato Ketchup (USA) | 3.0 | 76 | 8 | 5 | 6 | 5 |
| Instant meal (Swiss) | 0.6 | 76 | 8 | 5 | 6 | 5 |
| Sauce (Italy) | 3.0 | 93 | 5 | <1 | 3 | <1 |
| Canned tomatoes | 7.10 | 84 | 5 | 3 | 5 | 3 |

(Schierle et al., Content and isomeric ratio of lycopene in food and human blood plasma. Food chem. 59(3), 459-465 (1996)

Bioactivity potency depends on the extent of the isomerisation and oxidation as well as the stability when the tomato-based products are subjected to processing during storage. Heat, light, acids and other factors have been reported to cause isomerisation. A true assessment of the quality and health benefits of processed tomato based foods depends not only on the lycopene content but also on the distribution of isomers. Controlling lycopene isomerisation behaviour during production and storage of tomato products can benefit in improved product colour and quality.

Thermal processing: Heat treatment clearly increases the percentage of cis-isomer. Heating tomato-based foods in oil had a bigger effect on isomerisation than heating in water. Not only duration and temperature of heat treatment but also the food matrix components such as oil or fat influence the lycopene isomerisation.

Effects of dehydration: Dehydration method shows a significant increase in cis-isomer and simultaneous decrease in all-trans isomers. In osmotic treatment predominant mechanism is isomerisation while air-drying isomerisation and oxidation are the two factors affecting the total lycopene content and biological potency. Dehydration and increase of surface area generally leads to poor stability. Osmotic solution (with sugar) remaining on the surface layer of tomato prevents oxygen from penetrating and oxidizing lycopene. Therefore, osmotic treatment could reduce lycopene losses compared with other dehydration methods.

Lycopene degradation and colour change: Colour retention in tomato is better at lower temperature. The colour quality remains unchanged during osmotic treatment.

Lycopene stability during storage: The most important factor contributing to degradation is availability of oxygen during storage. With careful selection of storage condition to protect products from such facts as air by storing in an inert atmosphere or under vacuum, it is possible to retain initial colour levels during storage.

Antioxidant application: The main cause of damage to lycopene during food processing and storage is oxidation. Careful application of suitable antioxidants (Ethoxyquin, ascorbic acid, sodium acid pyrophosphate) at appropriate levels could have beneficial results. Low storage temperature, low light, low water activity, low moisture in storage will also have a limiting effect on the oxidation of lycopene.

Lycopene has a dual influence on production and quality as natural colour and nutrients for the food and pharma industry. Lycopene may be considered as "vitamin of the 21st century" because of its significant physiological effect on the human diet.

The fruit development processes leading up to fruit maturation may also have an effect on fruit components such as lycopene. Lycopene content in tomato fruit may be enhanced by improved techniques in fertilization, harvest time and variety selection. This focus may lead to higher quality tomato produced in green houses during winter.

The bio-availability of lycopene in foods is influenced not only by its isomeric forms, but also by the food matrix, the presence of sufficient bulk lipids for micellization of released lycopene and the presence of interfering factors in the lumen such as pectin and other dietary fibres. The degradation of lycopene is very important in tomato based food industry. Processing technology should be optimized to prevent lycopene oxidation and isomerisation.

Industrial production of lycopene from tomatoes is in high demand by pharmaceutical companies and for functional food development. At present, large quantity of skin and outer pericarp tissues are normally discarded as tomato processing waste in the peeling procedure of the tomato processing. Some new technologies such as membrane separation technology, supercritical fluid carbon dioxide technology and solvent extraction technology are being applied to scale up the lycopene production. High quality lycopene products that meet food safety regulation will offer potential benefits to the food industry. A successful commercialization of high value lycopene production may improve the competitiveness of tomato based products and lycopene products in the global market.

Numerous studies have shown that eating foods high in lycopene are beneficial in avoiding heart disease and several types of cancer such as lung, prostate, cervical, digestive tract and breast. Recent studies are looking at the effects of lycopene on such conditions as macular degenerative disease and serum lipid oxidation.

Those who support the above findings urge people to include lycopene in their diet for general good health. Good sources of lycopene are pink grapefruit, guava, watermelon, and rose hips, but the most common and perhaps the most potential is tomato.

Fresh tomatoes are an excellent source of lycopene, but cooked tomato products such as tomato and pizza sauce, tomato juice, tomato soup, and even ketchup, are more concentrated. For example, one fresh tomato contains 3.7 mg of lycopene, while one cup of tomato soup has 24.8 mg of lycopene. Because of the cis-form of lycopene in this cooked type of tomato product, the body can more easily absorb this lycopene.

Not everyone has accepted the benefits of lycopene. The world health regulatory agencies have not yet endorsed lycopene as a nutrient, but because of the promising results of early research, the health community is taking a serious look at the beneficial effects of lycopene in the diet. Of course, most health professionals agree that a diet rich with fruits and vegetables is part of a healthy lifestyle.

U.S. Pat. No. 5,837,311, Zelkha et al. (1998) describe a process for the extraction of lycopene from tomato pulp by extraction with solvents having delta H and delta P values. The oleoresin was obtained through this process having 2-10% lycopene content. However, the authors have not reported the purification step.

U.S. Pat. No. 5,897,866, Bombardelli et al. (1999) describe a process for the extraction of lycopene from tomato by using n-hexane and a chlorinated solvent. The process involved consists of extraction followed by column chromatographic separation which is tedious and industrial feasibility is questionable. There is no mention about the purity of isolated lycopene crystals.

Ausich et al. U.S. Pat. No. 5,858,700 (1999) reported the preparation of lycopene crystals from tomato and tomato products employing saponification with alkali and propylene glycol. The 90% lycopene crystals were obtained through this process with no mention of the isomeric form.

Kawaragi et al. U.S. Pat. No. 5,871,574 (1999) teaches the enzyme mediated extraction and purification of lycopene by using organic solvent. The product obtained through this process reported more than 10% lycopene content.

Konya et al. U.S. Pat. No. 6,331,652 (2001) reported a process for the preparation of lycopene. The process essentially is a chemical method involving multi stage reaction followed by column chromatographic separation and purification.

Estrella Decastro Antonio et al. EP 1201762 (2002) reported a process for the preparation of lycopene from fungal sources like blakeslea, choanephora or phycomyces. Ethyl acetate and ethyl alcohol and isopropyl alcohol were used for the extraction and purification, obtaining 94% purity of lycopene crystals though this process.

Giori et al. WO 03/079816 (2003) have described a process for the extraction and purification of lycopene from fresh tomato. The fresh tomatoes are crushed; water removed by vacuum distillation to obtain tomato concentrate. This concentrate is subjected to the extraction with water saturated ethyl acetate twice. This extract is washed with water and concentrated to obtain tomato oleoresin with 6% lycopene content. The concentrate is further washed with water, ethyl acetate and also by washing with ethanol (45 degrees C.) ageing and washing with ethyl acetate, to obtain crystalline lycopene with 95% purity.

Ho et al. WO 036125 (2006), have described a bio-process starting from tomato paste. (1) fermentation to remove sugars (2) enzyme mixtures to release the pigments from chloroplast and phytic acid, washed to remove heavy metals followed by sterilization and extraction with propane/butane gas yielding tomato extract containing 13% lycopene content.

Objectives of the Invention

Accordingly, the main object of the present invention is to provide an efficient process for the preparation of oleoresin containing lycopene and lycopene crystals for human consumption.

Another object of the present invention is to provide a process for obtaining a nutritional lycopene composition comprising at least 85% by weight of lycopene.

Another object is to provide lycopene crystals containing high amounts of trans-lycopene and trace amounts of cis-lycopene and other carotenoids.

Yet another object is to prepare oleoresin from any lycopene containing raw material including tomato waste, tomato skin, tomato paste and dehydrated tomato skin.

A further object is to make use of Generally Recognized as Safe solvents (GRAS solvents) for the extraction and purification of lycopene crystals.

Still another object is to obtain lycopene crystals free of residual solvent impurities.

Still another object is to provide a process for the preparation of oleoresin containing lycopene and lycopene crystals wherein the process is simple, convenient, economical and commercially feasible.

SUMMARY OF THE INVENTION

The process of the present invention is described herein below which is illustrative as shown in the examples and should not be construed to limit the scope of the present invention in any manner whatsoever.

Accordingly the present invention provides an efficient process for the preparation of lycopene crystals from lycopene containing oleoresin with at least 85% by weight lycopene enriched with trans-lycopene which comprises:

(a) admixing solvent free lycopene containing oleoresin with an aliphatic alcohol at elevated temperature;

(b) adding aqueous alkali solution in to the reaction mixture obtained in step (a) with agitation;

(c) maintaining said reaction mixture at a temperature of about 40 degree C. to about 60 degree C. for a time period sufficient to saponify the lipids and waxes;

(d) diluting the reaction mixture obtained in step (c) with water with agitation;

(e) filtering and collecting the lycopene crystals from said diluted reaction mixture and (f) washing the crystals with an aliphatic alcohol and drying the crystals under vacuum.

The ratio of lycopene containing oleoresin and aliphatic alcohol is 1:0.5 to 1:1 weight by volume.

The alkali used for preparing the alkali solution may be selected from sodium hydroxide, potassium hydroxide or mixtures thereof, preferably potassium hydroxide. The aqueous alkali contains 20 to 45% alkali weight by weight. The ratio of alcoholic lycopene containing oleoresin mixture and the aqueous alkali is in the range of 0.5 to 1.0 weight by weight.

The reaction mixture obtained after addition of alkali is maintained for a period of 1 to 3 hours at a temperature in the range of 40.degree. C. to 60.degree. C. to saponify the lipids and waxes.

The ratio of the saponified mixture and water is in the range of 0.5 to 1.

The crystals obtained after filtration from the diluted reaction mixture and after washing with aliphatic alcohol are dried under vacuum at 40 degree C.

The said solvent free lycopene containing oleoresin is prepared by a process which comprises:

(a) extracting lycopene from lycopene containing material with a mixture of non-polar and polar solvents;

(b) collecting the micelle and separating the lycopene containing non-polar layer;

(c) removing the solvents from the lycopene containing non-polar layer under reduced pressure and temperature of 50-60 degree C. to get solvent free lycopene containing oleoresin.

The lycopene containing oleoresin used in the process of the present invention can be prepared from any lycopene containing raw material, preferably tomato waste, tomato paste, fresh tomato or tomato powder. The non-polar solvent used in the process is hexane and the polar solvents are selected from aliphatic alcohol and ester solvents. The aliphatic alcohols may be selected from methyl alcohol, ethyl alcohol, isopropyl alcohol and mixture thereof. The ester solvent may be ethyl acetate. The said solvent free lycopene containing oleoresin has lycopene content in the range of 5-10% by weight with trans-lycopene in the range of 50-70% by weight. The ratio of the non-polar and polar solvents used for the preparation of lycopene containing oleoresin is 40:60 for wet lycopene containing raw material and 50:50 for dry lycopene containing raw material.

DESCRIPTION OF THE INVENTION

According to the present invention, a nutritional lycopene composition enriched in trans-lycopene which is suitable for human consumption is obtained from a lycopene containing material, preferably tomato fruit and its products, in a two step process involving: (1) preparation of lycopene containing oleoresin from lycopene containing materials and (2) preparation of lycopene crystals from lycopene containing oleoresin.

The details of the invention are as set forth.

All the technical and scientific terms used herein above have the meaning as commonly understood by a person ordinarily skilled in the art to which the invention belongs, unless otherwise defined in this specification.

Tomatoes are an excellent source of lycopene. Other sources include water melon, pink grapefruit and guava. There are many industrial tomato products available such as tomato puree, tomato paste, dehydrated tomato in powder form and by products like tomato skin along with fiber and seeds. Each of these products is a potential raw material for lycopene extraction and the extraction can be carried out with both wet and dry form of the raw material.

In the method of the present invention, lycopene containing oleoresin is prepared by admixing lycopene containing materials with a mixture of non-polar and polar solvents. A solvent mixture consisting of hexane: alcohol (40:60) for wet lycopene containing material and hexane: ethyl acetate (50:50) for dry lycopene containing material is used for lycopene extraction because it has good selectivity and the boiling points allow for complete removal of the solvent residues from the resulting extract. The ratio of wet lycopene containing material to the solvent mixture is 1:8 and 1:4 for dry lycopene containing material. A contact period of 2 hrs with continuous stirring is allowed for the ease of extraction and the separation of two layers. Upper red color non-polar layer contains lycopene and the lower polar layer contains moisture. The upper micelle non-polar layer is filtered through cotton and the solvent mixture containing lycopene is subjected to reduced pressure and elevated temperature of 50-60 degree C. to get a solvent free lycopene containing oleoresin having lycopene content of 5-10% by weight with trans-lycopene in the range of 50-70% by weight.

The said lycopene containing oleoresin, containing at least 5% by weight lycopene, is further admixed with an aliphatic alcohol and homogenized at elevated temperature of 60 degree C. for a period of 30 minutes. An aqueous alkali solution (45% by weight) is added to the reaction mixture and refluxed under heating for 1 hour to saponify the lipids and waxes present in the reaction mixture. The saponified reaction mixture is diluted with deionized water under stirring for effective separation of lycopene crystals. The diluted solution is filtered and the cake is washed with warm water to remove the alkali and other impurities, followed by washing with aliphatic alcohol to remove trace amounts of moisture. The red crystalline lycopene obtained is removed and dried under vacuum (30-40 degree C.).

The lycopene crystals can be further admixed and micronized with vegetable oil to form lycopene oil suspension containing less than 0.1 to 1 micron size particles with about 1 to 40% by weight of lycopene.

The lycopene crystals obtained can be alternatively embodied with permitted ingredients and binders to form lycopene powder dispersible in water with about 1 to 5% by weight of lycopene.

In an embodiment of the present invention the lycopene containing material is preferably fresh tomato, tomato waste, tomato paste or tomato powder.

The method of analysis consists use of spectrophotometer for determining the total lycopene content and HPLC for determining the trans-lycopene content. Lycopene content in a sample of tomato oleoresin or lycopene crystals dissolved in hexane was determined at 470 nm, using Perkin Elmer 1700 spectrophotometer and the concentration of lycopene was calculated using a molar extinction coefficient of 3450 in hexane. The all trans-lycopene content in the oleoresin or in lycopene crystals was quantified using the HPLC modified method of Ishida et al.

The composition of the present invention is particularly beneficial in warding off heart disease and various types of cancer. The present invention, more particularly, provides a lycopene composition enriched in 50-90% by weight of trans-lycopene which is not otherwise naturally available.

The following examples are given by the way of illustration of the present invention and therefore should not be construed to limit the scope of the present invention.

Example 1

Preparation of Tomato Oleoresin from Wet Tomato Skin

A weighed quantity of tomato skin (300 g, 0.022% weight lycopene) is extracted with 2400 ml of hexane-ethanol solvent mixture in the ratio of 40:60 with a stirring period of 2 hrs. After stirring, the micelle is decanted to obtain a residue. The residue is twice extracted with 1800 ml of hexane-ethanol solvent mixture in the ratio of 40:60 with a stirring period of 2 hrs. The micelle thus obtained is combined together resulting in the formation of two layers. The upper layer is the hexane layer containing lycopene whereas the lower layer is the aqueous layer. The upper layer is then separated from the lower layer, filtered through cotton and concentrated by drying under vacuum at a temperature of 50-60 degree C. to obtain 0.52 g oleoresin. The oleoresin obtained was analyzed by spectrophotometer and found to contain 10.13% lycopene. The relative area percentage of trans-lycopene was 68.43% by HPLC analysis.

Example 2

Preparation of Tomato Oleoresin from Wet Tomato Paste

A weighed quantity of tomato paste (300 g, 0.0845% weight lycopene) was extracted with 1500 ml of hexane-ethanol solvent mixture in the ratio of 40:60 with a stirring period of 2 hrs. After stirring, the micelle was decanted to obtain a residue. The residue was twice extracted with 1800 ml of hexane-ethanol solvent mixture in the ratio of 40:60 with a stirring period of 2 hrs. The micelle thus obtained was combined together resulting in the formation of two layers. The upper layer is the hexane layer containing lycopene whereas the lower layer is the aqueous layer. The upper layer was then separated from the lower layer, filtered through cotton and concentrated by evaporation under vacuum at a temperature of 50-60 degree C. to obtain 2.4 g oleoresin. The oleoresin obtained was analyzed by spectrophotometer and was found to contain 10.30% lycopene content. The relative area percentage of trans-lycopene was 72.42% by HPLC analysis.

Example 3

Preparation of Tomato Oleoresin from Dehydrated Tomato Skin

A weighed quantity 100 g of powdered dehydrated tomato skin (100 g, 0.22% weight lycopene) was extracted with 400 ml of hexane-ethyl acetate solvent mixture in the ratio of 50:50 with a stirring period of 2 hrs. After stirring, the micelle was decanted to obtain a residue. The residue was extracted four times with the same solvent mixture. The micelle thus obtained was combined together, filtered and concentrated by evaporating under vacuum at a temperature of 50-60 degree C. to obtain 2.3 g oleoresin. The oleoresin obtained was analyzed by spectrophotometer and was found to contain 6.10% lycopene content. The relative area percentage of trans-lycopene was 62.42% by HPLC analysis.

Example 4

Preparation of Lycopene Crystals from Tomato Oleoresin

A weighed quantity of tomato oleoresin (25 g, 6-7% weight lycopene) was homogenized with 25 ml ethanol at a temperate of 50 degree C. for 30 minutes under stirring. Aqueous potassium hydroxide (45% by wt.) was added to the homogenized solution. The mixture was then saponified by heating at temperature of 58-62 degree C. with continuous agitation for a period of 1-3 hrs. The resultant saponified mixture was diluted with 200 ml de-ionized water at the same temperature with agitation for 30 minutes and filtered under hot condition. The precipitate was then washed with the water at a temperature of 58-62 degree C. for a period of one hour. The precipitated mass was filtered and the bed was washed with 25 ml ethanol. The precipitate obtained was vacuum dried to obtain 1.1 g lycopene crystals containing 97% lycopene. The relative area percentage of trans-lycopene content was 95.53% by HPLC analysis.

Example 5

Preparation of Lycopene Crystals from Tomato Oleoresin

A weighed quantity of tomato oleoresin (25 g. containing 7-8% weight lycopene) was homogenized with 25 ml ethanol at a temperate of 50 degree C. for 30 minutes under stirring. Aqueous potassium hydroxide (45% by wt.) was added to the homogenized solution. The mixture was then saponified by heating at temperature of 58-62 degree C. with continuous agitation for a period of 1-3 hrs. The resultant saponified mixture was diluted with 200 ml de-ionized water at the same temperature with agitation for 30 minutes and filtered under hot condition. The precipitate was then washed with water at a temperature of 58-62 degree C. for a period of one hour. The precipitated mass was filtered and the bed was washed with 25 ml ethanol. The precipitate obtained was vacuum dried to obtain 1.4 g lycopene crystals containing 87.8% weight lycopene. The relative area percentage of trans-lycopene was 94.45% by HPLC analysis.

Advantages of the Invention

The process results in the formation of a nutritional lycopene composition comprising at least 85% by weight of lycopene.

The lycopene crystals obtained from the said process contain high amounts of trans-lycopene and trace amounts of cis-lycopene and other carotenoids.

The said oleoresin is prepared from any lycopene containing raw material including tomato waste, tomato skin, tomato paste and dehydrated tomato skin.

The extraction and purification of lycopene crystals are done by using Generally Recognized as Safe solvents (GRAS solvents).

The lycopene crystals obtained are free of any residual solvent impurities.

The process used for preparation of lycopene containing oleoresin and lycopene crystals is simple, convenient, economical and commercially feasible.

The production of commercial grade lycopene crystals with high content of trans-lycopene makes it ideal and suitable for human consumption, useful as anti-oxidant, for applications in prevention of cancer and macular degenerative diseases and as a food/feed colorant.

We claim:

1. A process for the preparation of a lycopene crystals composition with at least 85% by weight lycopene, wherein the lycopene crystals composition comprises 50% or more by weight of trans-lycopene, comprising the steps of:
   (a) admixing solvent free lycopene containing oleoresin with ethanol to obtain a reaction mixture;
   (b) adding aqueous alkali solution to the reaction mixture obtained in step (a) with agitation to obtain a mixture;
   (c) maintaining the mixture obtained in step (b) at a temperature of around 40 degree C. to about 60 degree C. for a time period sufficient to saponify the lipids and waxes;
   (d) diluting the mixture after step (c) with water under agitation to obtain a diluted reaction mixture;
   (e) filtering and collecting lycopene crystals from the diluted reaction mixture and
   (f) washing the lycopene crystals with ethanol and drying the lycopene crystals under vacuum to obtain the lycopene crystals composition that includes at least 85% by weight lycopene, wherein the lycopene crystals composition comprises 50% or more by weight trans-lycopene.

2. The process as claimed in claim 1, wherein the ratio of solvent free lycopene containing oleoresin and ethanol used in step (a) is 1:0.5 to 1:1 weight by volume.

3. The process as claimed in claim 1, wherein the aqueous alkali solution used in step (b) comprises 20 to 45% weight by weight of alkali.

4. The process as claimed in claim 1, wherein the aqueous alkali solution includes an alkali, wherein the alkali is selected from at least one of the group consisting of potassium hydroxide, sodium hydroxide, and mixtures thereof.

5. The process as claimed in claim 1, wherein during step (c), the mixture is maintained for a period of 1 to 3 hrs.

6. The process as claimed in claim 1, wherein, in step (b), the ratio of the reaction mixture obtained in step (a) and aqueous alkali solution is in the range of 0.5 to 1.0 weight by weight.

7. The process as claimed in claim 1, wherein, in step (d), the ratio of the mixture and water is in the range of 0.5 to 1.0 weight by volume.

8. The process as claimed in claim 1, wherein the drying of step (f) is carried out at 40 degree C. under vacuum.

9. The process as claimed in claim 1, wherein the lycopene crystals composition contains at least 80% by weight trans-lycopene and the remainder of the lycopene crystals composition being cis-lycopene and other carotenoids.

10. The process as claimed in claim 1, wherein the lycopene crystals composition contains at least 90% by weight trans-lycopene and the remainder of the lycopene crystals composition being cis-lycopene and other carotenoids.

11. The process as claimed in claim 1, wherein the lycopene crystals are admixed and micronized with vegetable oil to form a lycopene oil suspension containing less than 1 micron size particles with about 1 to 40% by weight of lycopene relative to the total weight of the lycopene oil suspension.

12. The process as claimed in claim 1, wherein the lycopene crystals are admixed and micronized with vegetable oil to form a lycopene oil suspension containing less than 0.1 micron size particles with about 1 to 40% by weight of lycopene relative to the total weight of the lycopene oil suspension.

13. The process as claimed in claim 1, comprising forming the lycopene crystals into a lycopene powder dispersible in water with about 1 to 5% by weight of lycopene.

* * * * *